(12) United States Patent
Lewis et al.

(10) Patent No.: US 7,159,333 B2
(45) Date of Patent: Jan. 9, 2007

(54) USE OF PERCARBAMIC ACIDS AND DIACYL PERCARBAMATES AND PRECURSORS THEREFOR

(75) Inventors: David Malcolm Lewis, Otley (GB); Jiming Yao, Toronto (CA); Jerry S. Knapp, Pudsey (GB); Jamie Anthony Hawkes, Bromsgrove (GB)

(73) Assignee: The University of Leeds, West Yorkshire (GB)

( * ) Notice: Subject to any disclaimer, the term of this patent is extended or adjusted under 35 U.S.C. 154(b) by 411 days.

(21) Appl. No.: 10/344,889

(22) PCT Filed: Aug. 16, 2001

(86) PCT No.: PCT/GB01/03656

§ 371 (c)(1),
(2), (4) Date: Sep. 6, 2003

(87) PCT Pub. No.: WO02/16538

PCT Pub. Date: Feb. 28, 2002

(65) Prior Publication Data

US 2004/0055092 A1    Mar. 25, 2004

(30) Foreign Application Priority Data

Aug. 18, 2000 (GB) ................... 0020489.1

(51) Int. Cl.
*C11D 3/395* (2006.01)
(52) U.S. Cl. .......................... 34/329; 510/375
(58) Field of Classification Search ............... None
See application file for complete search history.

(56) References Cited

U.S. PATENT DOCUMENTS

| | | | |
|---|---|---|---|
| 3,965,015 A | 6/1976 | Bauman | |
| 4,063,923 A | 12/1977 | Han | |
| 4,259,383 A * | 3/1981 | Eggensperger et al. | 428/72 |
| 4,272,413 A | 6/1981 | Bauman | |
| 6,821,302 B1 * | 11/2004 | Au et al. | 8/405 |
| 2004/0055092 A1 * | 3/2004 | Lewis et al. | 8/115.51 |

FOREIGN PATENT DOCUMENTS

| CA | 2083319 | 11/1992 |
|---|---|---|
| EP | 0 333 350 A2 | 9/1989 |
| EP | 0 543 175 A1 | 5/1993 |
| JP | 52124758 | 10/1977 |
| JP | 62001793 | 1/1987 |
| JP | 9053096 | 2/1997 |
| JP | 09-087685 | 3/1997 |
| JP | 9059690 | 3/1997 |
| JP | 9087679 | 3/1997 |
| JP | 9087685 | 3/1997 |
| WO | WO 2002-16538 A * | 2/2002 |

OTHER PUBLICATIONS

Houben-Weyl, methoden der organischen Chemie (Methods of Organic Chemistry), vol. E4, pp. 362-364.
Houben-Weyl, methoden der organischen Chemie (Methods of Organic Chemistry), vol. E4, pp. 181-189.
Lapshin et al., "Infrared Spectra of Some Percarbonates and Percarbamates," USSR Zhumal Organicheskoi Khimii, 4(b), pp. 952-54 (1968).
Beilstein Database File XFIRE, XP 002184692.

* cited by examiner

*Primary Examiner*—John R. Hardee
(74) *Attorney, Agent, or Firm*—Goodwin Procter LLP

(57) ABSTRACT

The invention provides a method of treatment of a material, comprising contacting said material with a percarbamic acid and/or diacyl percarbamate. Preferably the percarbamic acid has formula (I), where R represents an optionally substituted alkyl, aryl, heteroaryl, cycloalkyl or non-aromatic heterocyclic group, a hydrogen atom, or a group having formula (1a), where each $R^2$ independently represents a hydrogen atom or an alkyl group; and m=0 to 30. The method provides effective bleaching agents and resterilizing agents and or bacteriocidal agents over a wide range of pH and temperatures, for a wide range of applications. Compositions comprise formula (II), whereby R is H or alkyl and L is a moiety displaced by —OOH, and hydrogen peroxide or per hydroxy anion or a precursor therefor

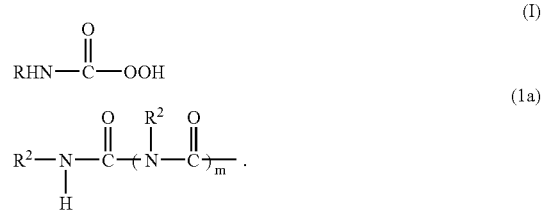

22 Claims, No Drawings

USE OF PERCARBAMIC ACIDS AND DIACYL PERCARBAMATES AND PRECURSORS THEREFOR

The present invention relates to the preparation and application of percarbamic acids and diacyl precarbamates, in particular to their use in bleaching, sterilisation and purification processes. The invention further relates to certain novel precursors for such acids.

Many bleaches are based on hydrogen peroxide chemistry. Convenient solid carriers of hydrogen peroxide favoured by the laundry industry include sodium percarbonate or perborate, these compounds reacting immediately with water to give free hydrogen peroxide. Hydrogen peroxide functions as an excellent bleach at temperatures greater than 60° C. and at pH greater than 10. In order to facilitate low temperature bleaching under normal household washing temperatures of less than 60° C. bleach activators are used. Usually bleach activators form the reactive bleach, commonly peracetic acid, by reaction of O-acetyl or N-acetyl species with alkaline hydrogen peroxide.

Examples of bleach activators commonly used in household laundry operations include N,N,N',N'-tetraacetylethylenediamine (TAED), sodium nonanoyloxybenzene-4-sulphonate, (SNOBS), glucose-pentaacetate (GPA), di-N-acetyldimethylglyoxin (ADMG) and 1-phenyl-3-acetylhydantoin (PAH). Of the examples listed TAED, which forms peracetic acid, has had the most impact, followed by SNOBS, which forms pernonanoic acid. Such compounds are exemplified in GB 836988, GB 907356, EP 98129, U.S. Pat. Nos. 2,898,181, 3,163,606 and EP 120591.

A disadvantage of these compounds is that they do not work effectively at temperatures lower than about 40° C. or at acidic and neutral pH.

Recent research has described the use of peramidic acid (NH$_2$—(C=NH)OOH), formed from the reaction of cyanamides, dicyanamides and their acid salts with hydrogen peroxide, for laundry bleaching. Examples are disclosed in U.S. Pat. Nos. 4,086,177, 3,756,774 and EP 819673. In each of these examples the use of peramidic acid as the bleaching agent enables a pH of between 7.5–13 and temperatures of 20–60° C. to be used for laundry washing. However in each case the highest activity is still obtained at pH 9–13 and temperatures of 40°–80°.

Furthermore cyanamides, dicyanamides and their acid salts are potentially highly toxic, and must therefore be thoroughly rinsed from laundry washed using these compounds as bleach activators.

In JP 9-87685 an aqueous alkaline solution of alkali metal or ammonium cyanate salts, in combination with hydrogen peroxide, is disclosed for use in bleaching/deodorising sports shoes. The optimum pH for the process is 9–11, similar to the other bleaching processes described above., There is no mention of the mechanism of bleaching/deodorising.

EP 543175 discloses the use of cyanate salts and alkaline hydrogen peroxide solutions at pH>10 for the bleaching of paper pulp. However the disclosure suggests only a small improvement of whiteness.

Surprisingly it has been found that percarbamic acids, including percarbamic acid itself and N-substituted percarbamic acids, are effective bleaching agents and/or sterilising and/or bactericidal agents over a wide range of pH and temperatures, and are suitable for a wide range of applications. When the percarbamic acid is formed it is believed that it may be accompanied by the part production of a corresponding diacyl precarbamate.

Accordingly, the present invention provides a method of treatment of a material, comprising contacting said material with a percarbamic acid and/or diacyl percarbamate, preferably in aqueous solution. Preferably the material as contacted with a percarbamic acid. Percarbamic acids and suitable N-substituted percarbamic acids include compounds of general formula

where R represents an optionally substituted alkyl, aryl, heteroaryl, cycloalkyl or non-aromatic heterocyclic group, a hydrogen atom, a group having the formula

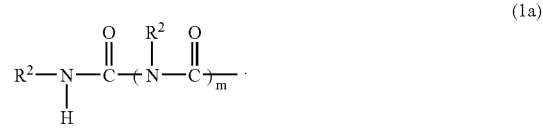

where each $R^2$ independently represents a hydrogen atom or an alkyl group; and m=0 to 30, preferably 0 to 10, most preferably 0 to 5.

Suitably when R is a group having the formula (1a), each $R^2$ is identical. Most suitably when R is a group having the formula (1a) each $R^2$ is a hydrogen atom.

Most preferably R represents an alkyl group or, especially, a hydrogen atom.

We make no claim to methods described in JP 9-87685 or EP 543175. Thus in the event that the methods described in those documents are shown to make percarbamic acids in situ, we may disclaim a) methods of treating sports shoes, employing hydrogen peroxide or peroxidate and an alkali metal or ammonium cyanate at concentration 0.1–30% w/w on treatment solution at a pH in the range 7 to 13; and b) methods of bleaching paper pulp which employ alkali metal cyanates and hydrogen peroxide at pH>10. Alternatively we may in that event claim our method as being for treatment of materials other than sports shoes and paper pulp.

Suitable diacyl percarbamates include compounds having the formula

wherein R is as defined above.

The method of treatment is preferably carried out in the pH range 3 to 11, more preferably 4 to 9 and most preferably 5 to 8.

The method of treatment is preferably carried out at a temperature in the range 0° C. to 95° C., more preferably 0° C. to 70° C., and most preferably 20° C. to 40° C.

Materials to be treated may be organic fibres including cellulose, lignin and hair, inorganic fibres, textile materials including cotton, wool and synthetic textiles, metal surfaces, wood surfaces, ceramic surfaces, plastics surfaces, and liquids, especially aqueous liquids.

The method of treatment is preferably bleaching, for example hair bleaching, textile bleaching, including household laundry and industrial textile bleaching, dye bleaching for both solutions and dyed surfaces, and pulp and paper bleaching.

Alternatively the method of treatment may be sterilisation of surfaces or contaminated water/aqueous solutions, including waste water streams containing dyestuffs and humic components.

A preferred method of the present invention is the bleaching of clothes, especially during washing thereof. In such methods the aqueous solution also contains detergency agents.

Another preferred method is bleaching of human hair.

Preferably the percarbamic acid and/or diacyl percarbamate is generated in situ. By in situ, we mean that it is generated during or shortly before the method of treatment.

Compounds of general formula (I) in which R represents a hydrogen atom may be prepared, suitably in situ, by the admixture in an aqueous composition of an alkali metal or ammonium cyanate and hydrogen peroxide (or the perhydroxy anion). The reaction to produce the compound of formula (I) is believed to proceed via isocyanic acid $HN=C=O$.

Compounds of formula (I) in which R represents a hydrogen atom may also be prepared, suitably in situ, by the admixture in an aqueous composition of formamide and hydrogen peroxide (or the perhydroxy anion). Again, the reaction is believed to proceed via isocyanic acid.

A preferred method of generating, preferably in situ, compounds of general formula (I) in which R is a hydrogen atom or an alkyl group comprises reacting a carbamat compound of the general formula

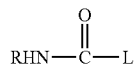 (II)

with hydrogen peroxide (or the perhydroxy anion) where R is as defined above and L is a moiety displaced by the anion

The preferred temperature and pH conditions for these three methods are the same as the preferred conditions set out above for the method of treatment.

Preferably L is selected from a phosphonate, phosphinate, thiourea or quaternary ammonium group; or from groups of the formula —$SO_3M$ where M represents a hydrogen atom, or an alkali metal atom, or an ammonium group; or from groups of the formula

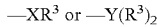

where X represents an oxygen or sulphur atom, Y represents a nitrogen atom, and $R^3$ is selected from hydrogen, optionally substituted alkyl, optionally substituted aryl, optionally substituted amino, cyano, hydroxyl and optionally substituted alkylcarbonyl groups wherein when L is —$Y(R^3)_2$ each $R^3$ group may be the same or different and is independently selected from the above list, or the groups $R^3$ and Y may together represent an optionally substituted heteroaryl or non-aromatic heterocyclic group.

Suitable substituents of an aryl or heteroaryl group include halogen, especially fluorine, chlorine and bromine atoms, and nitro, cyano, hydroxyl, alkyl, haloalkyl haloalkoxy, alkoxyalkyl, aryloxy, alkoxy, alkoxyalkoxy, ammo, mono and di-alkylamino, aminoalkyl, mono- and di-alkylaminoalkyl, amido, mono- and di-alkylamido groups and groups of formula —$SO_3M$ or —COOM where M is as defined above. An especially preferred substituent of an aryl group is $SO_3M$.

Any substituted aryl or heteroaryl group may suitably be substituted by one to three substituents, preferably by one substituent Preferred substituents of an alkyl group or of an alkyl moiety within a larger group or of a cycloalkyl or non-aromatic heterocyclic group include halogen, especially fluorine, chlorine or bromine atoms, and nitro, cyano, amidothio (—S—$CONH_2$), amidoamino (—NH—$CONH_2$), hydroxy, alkoxy, haloalkoxy, —COOM, alkoxycarbonyl amino and mono- and di-alkylamino and —$SO_3M$ groups, where M is as defined above.

Preferred substituents of an amino group (including of a larger group such as amido) include alkyl, cyano, hydroxyl, alkoxy, amino, amido, thioamido (—$CSNH_2$), aminosaccharide, polyaminosaccharide groups (for example glucosamino and polyglucosamino groups). Preferably an amino group is unsubstituted or mono-substituted, or disubstituted by two alkyl, especially methyl, groups.

Preferred heteroaryl or non-aromatic heterocyclic groups contain 1–3 hetero ring atoms selected from oxygen, sulphur or nitrogen. Preferred groups have at least one ring nitrogen atom. Preferred heteroaryl and non-aromatic heterocyclic groups include pyrazine and pyridine groups which are unsubstituted or substituted by a single group selected from —COOM and —$CONH_2$, where M is as defined above; piperidine and morpholine groups which are unsubstituted or substituted by a single $C_{1-4}$ alkyl group; and bicyclic non-aromatic heterocycles containing one or two nitrogen atoms, for example azabicyclooctane and diazabicyclooctane.

A preferred sub-class of groups L is those of formula —$SO_3M$ where M is as defined above.

A preferred sub-class of groups L is those of formula —SX where X represents a cyano group, $SO_3M$ (where M is defined above) or an optionally substituted $C_{1-6}$ alkyl group (preferably unsubstituted or substituted by one to three substituents independently selected from —COOM, —$SO_3M$, hydroxyl, amidothio, optionally substituted amino (preferably $NH_2$ or —NH—$CONH_2$), optionally substituted alkoxy (preferably unsubstituted), optionally substituted amido (preferably —$CONH_2$) and —COOY, where M is as defined above and Y is an optionally substituted (preferably unsubstituted) alkyl group).

Especially preferred groups L are —SCN and —$SO_3M$. In relation to any of the foregoing definitions, preferably M represents hydrogen or an alkali metal atom; and especially hydrogen or sodium.

A noteworthy sub-class of groups L is those of formula —OX' where X' represents an optionally substituted (preferably unsubstituted) alkyl group; an optionally substituted (preferably unsubstituted) aryl group or an optionally substituted (preferably unsubstituted) alkylcarbonyl group, or a group —CHO or —OCN. A preferred group L of formula —OX' is —O—$PhSO_3M$ where M is defined above.

A noteworthy sub-class of groups L is those of formula —NX"X''' where, X" and X''' may both be alkyl groups or X" may be a hydrogen atom and X''' may be a cyano, alkyl, hydroxyl, amido, amino, aminosaccharide or polyaminosaccharide group.

A noteworthy sub-class of groups L is those of formula —P(=O)R'R" where R' represents hydroxy and R" represents hydrogen or hydroxy or amido.

A noteworthy sub-class $Q^+$ of groups L is those connected to the C=O group by an $N^+$ atom, the group Q being a quaternary ammonium moiety formed from a tertiary amine, or a heteroaryl or non-aromatic heterocyclic group as detailed above.

Examples of suitable groups L include:

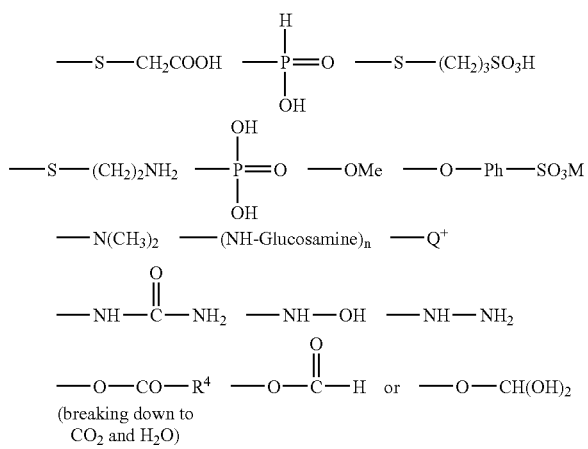

where R⁴ is an alkyl group or a hydrogen atom
and, especially
$SO_3M$ (especially $SO_3H$ and $SO_3Na$)

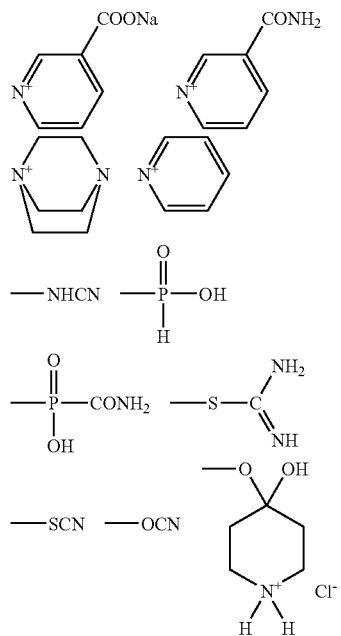

It should be noted that suitable compounds NHR—CO—L include compounds which may have more than one group NHR—CO—, and so many offer more than one point of attack to the peroxyanion. One example of compound of this type is biuret.

Compounds of formula (II) in which R represents hydrogen may be prepared by a reaction employing an alkali metal or ammonium cyanate and a compound HL where L is as defined above. An alkali metal cyanate, notably sodium cyanate, is preferred. The reaction is believed to proceed via isocyanic acid HN=C=O. The resulting compounds (II) may be isolated but if it is wished they may be contacted with hydrogen peroxide, or the perhydroxy anion, in situ to effect the treatment method.

Preferably the process employing an alkali metal or ammonium cyanate and a compound of formula HL is performed in the presence of a solvent, more preferably in aqueous solution. Suitably the pH of the reaction mixture is maintained between 2 and 10, most preferably between 4 and 8. The pH needed will, however, depend on the nature of L.

Where L is a sulphur-containing leaving group the pH is preferably maintained between 4 and 5 for the duration of the reaction.

Where L is a tertiary amine containing leaving group, such as pyridine, the pH is preferably maintained between 6.5 and 7.5 for the duration of the reaction.

Where L contains an alcoholate residue the pH is preferably maintained between 7 and 8 for the duration of the reaction.

Preferably the reaction is carried out at a temperature between 0° C. and 100° C., more preferably between 10° C. and 50° C., and most preferably at ambient temperature.

Compounds of formula (II) in which R is not hydrogen may be prepared by reacting an organic isocyanate R—N=C=O with a selected compound HL in the presence of an organic solvent, where L is as defined above. The N-substituted carbamate compounds (II) may be isolated but if it is wished they may be contacted with hydrogen peroxide, or the perhydroxy anion in situ to effect the treatment method. In such cases an organic solvent miscible with water is selected, suitable solvents including isoproponol, acetone, dimethyl formamide and dimethyl sulphoxide.

In accordance with a further aspect of the invention there is provided a washing or bleaching or sterilizing or bactericidal composition comprising a compound of formula (II) and hydrogen peroxide or the perhydroxy anion or a precursor therefor. The composition may include a solid concentrate or a liquid concentrate. The composition may when intended for washing or bleaching contain detergent components. A preferred composition comprises a solid, preferably granular, clothes washing composition, comprising a detergent, a compound of formula (m and a compound which generates perhydroxy anions in water.

Certain compounds of formula (I) are believed to be novel and accordingly constitute a further aspect of the invention. In this aspect, the invention provides compounds of formula

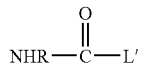

where R is as defined above (but is preferably hydrogen)
where L' represents a group selected from the following:

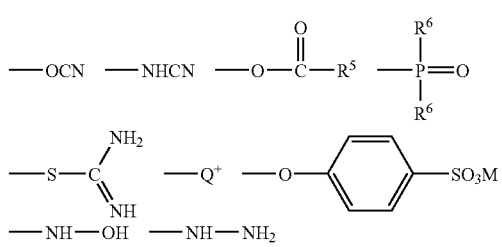

and where $R^5$ is an optionally substituted alkyl group and each group $R^6$ is selected independently from H, OH and $CONH_2$, and $Q^+$ is as defined above.

Such compounds may be prepared as described above, and such methods applied for the preparation of novel compounds constitutes a further aspect of the present invention.

The following examples are used to illustrate the invention. The identity of each of the activators whose preparation was described was confirmed for their IR spectra using a Perkin Elmer 1725 Infrared Fourier Transform Spectrometer, and by microanalysis. Chemicals were obtained from Aldrich unless stated otherwise. Hydrogen peroxide used was 27.5% (w/w) grade; sodium cyanate used was 96% grade.

EXAMPLE 1

Preparation of Activator 1 (ASP 1)

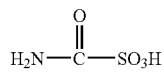
[ASP1]

Sodium cyanate (5 g, 0.077 mol) was dissolved in water (50 ml) and stirred for 5 minutes at room temperature; sodium bisulphite (8 g, 0.077 mol) was added to this solution. After the sodium bisulphite dissolved, the pH was adjusted pH to 5 using hydrochloric acid (1 M). The reaction was carried out at room temperature, the pH being maintained at 5.0~5.5. by the addition of hydrochloric acid. When the pH of the solution became stable, the reaction was stopped. The product was precipitated by the addition of 200 ml of ethanol to the reaction solution; the solid was filtered off and dried in ambient air.

An alternative effective preparation was to dissolve sodium metabisulphite (4 g, 0.077 mol) in water 5 ml and then to quickly add sodium cyanate (5 g, 0.077 mol) maintaining the pH at 4.5 (acetic acid addition) at room temperature. After 10 minutes the product was precipitated using ethanol as above.

EXAMPLE 2

Preparation of Activator 2 (ASP 2 and 2A)

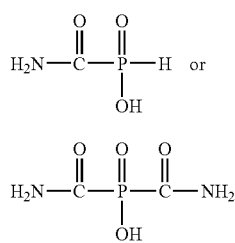
[ASP2]

[ASP2A]

Sodium cyanate (5 g, 0.077 mol) was dissolved in water (50 ml) and stirred for 5 minutes; then the pH of the cyanate solution was adjusted to 5 using hydrochloric acid (1 M); Hypophosphorous acid (5 g, 50% (w/w) solution, 0.0038 mol) was dissolved in water (20 ml) and gradually added to the stirred cyanate solution over 1 hour, the pH was maintained at 5. After the addition of hypophosphorous acid, the reaction was continued at room temperature until the pH became stable; the reaction was then stopped. During the reaction, a solid product precipitated; when the reaction finished, this solid was filtered off and dried in ambient air.

A double substitution reaction can occur to give a mixture of products (ASP 2 and ASP 2A); more quantitative yields of ASP 2A can be achieved by giving a larger amount of sodium cyanate. In this example ASP 2A is the predominant product.

EXAMPLE 3

Preparation of Activator 3 (ASP 3)

[ASP3]

Sodium cyanate (5 g, 0.077 mol) was dissolved in water (501 ml) and stirred for 5 minutes at room temperature; then the pH of the cyanate solution was adjusted to 5 using hydrochloric acid (1 M). Cyanamide (3.2 g, 0.077 mol) solid was gradually added to the stirred cyanate solution over 1.5 hour, the pH being maintained at 5. After the addition of cyanamide, the reaction was continued at room temperature and at pH 5~5.5. When the pH of the solution became stable, the reaction was stopped. During the reaction a solid product precipitated; when the reaction finished, this solid was filtered off and dried in ambient air.

EXAMPLE 4

Tea-Stained Cotton Fabric Bleaching using Bleach Activators ASP 1 to ASP 3 from Examples 1 to 3.

Tea-stained cotton fabric was prepared by the following method:

Three small tea bags of British-style "brown" tea were placed in 1000 ml of water and boiled for 15 minutes. A plain weave cotton fabric was impregnated by adding this solution (wet pick-up 100%) and this fabric was allowed to dry in ambient air. This fabric was then left in a laboratory oven for 60 minutes at 60° C.

The bleach solution was made up as follows:

| | |
|---|---|
| Hydrogen peroxide (100%) | 5 g/l |
| Bleach activator | 3 g/l |
| pH buffer | |
| Goods to liquor ratio | 1:10 |
| pH buffer used was: | pH 5 or 7 - sodium dihydrogen phosphate (0.1 M) and sodium hydroxide (0.1 M) |
| | pH 10 - sodium carbonate |

Tea stained fabric, as described above, and bleach solution were put in to a 100 cm³ is sealed stainless steel dyepot and placed in a laboratory dyeing machine (Rotadyer). The bleaching process was cared out for 45 minutes at the selected temperature. After bleaching, the fabric was washed thoroughly in tap water and dried in ambient air. The CIE whiteness values of the tea stained starting fabric was measured, and found to be −34.4.

TABLE 1

CIE whiteness values of fabric bleached at pH 5 at different temperatures

| Bleaching Species | CIE Whiteness | | |
|---|---|---|---|
| | 20° C. | 50° C. | 95° C. |
| $H_2O_2$ | 24.5 | 35.5 | 62.2 |
| $H_2O_2$ + ASP 1 | 42.8 | 44.1 | 77.0 |
| $H_2O_2$ + ASP 2/2A | 23.0 | 34.9 | 63.7 |
| $H_2O_2$ + ASP 3 | 21.2 | 41.4 | 65.2 |

TABLE 2

CIE whiteness values of fabric bleached at pH 7 at different temperatures

| Bleaching Species | CIE Whiteness | | |
|---|---|---|---|
| | 20° C. | 50° C. | 95° C. |
| $H_2O_2$ | 39.1 | 43.1 | 75.9 |
| $H_2O_2$ + ASP 1 | 64.2 | 65.7 | 84.8 |
| $H_2O_2$ + ASP 2/2A | 37.6 | 47.6 | 74.4 |
| $H_2O_2$ + ASP 3 | 38.3 | 52.9 | 73.0 |

TABLE 3

CIE whiteness values of fabric bleached at pH 10 at different temperatures

| Bleaching Species | CIE Whiteness | | |
|---|---|---|---|
| | 20° C. | 50° C. | 95° C. |
| $H_2O_2$ | 61.8 | 60.7 | 77.8 |
| $H_2O_2$ + ASP 1 | 72.0 | 74.0 | 80.6 |
| $H_2O_2$ + ASP 2/2A | 58.1 | 65.7 | 85.1 |
| $H_2O_2$ + ASP 3 | 57.6 | 74.4 | 85.1 |

EXAMPLE 5

Preparation of Activator 5 (ASP 7)

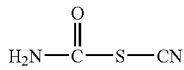

[ASP7]

Sodium cyanate (5 g, 0.077 ml) was dissolved in water (50 ml) and stirred for 5 minutes at room temperature; sodium thiocyanate (8.1 g, 0.1 mol) was added to this solution. After the sodium thiocyanate dissolved, the pH was adjusted to 5 using acetic acid. The reaction was carried out at room temperature, the pH being maintained at 5.0~5.5 by the addition of acetic acid; when the pH of the solution became stable, the reaction was stopped. The product was precipitated by the addition of 300 ml of ethanol to the reaction mixture. The solid was filtered off and dried in ambient air.

EXAMPLE 6

Preparation of Activator 6 (ASP 8)

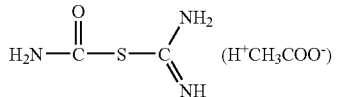

[ASP8]

Sodium cyanate (5 g, 0.077 ml) was dissolved in water (70 ml) and stirred for 5 minutes; then the pH of the cyanate solution was adjusted to 5 using acetic acid. Thiourea solid (7.6 g, 0.1 mol) was added to the stirred cyanate solution over 1 hour; the pH was maintained at 5~5.5. After the addition of thiourea, the reaction was continued at room temperature until the pH became stable; the reaction was then stopped. The product (an isothiouronium salt) was precipitated by the addition of 300 ml of ethanol to the reaction mixture; the solid was filtered off and dried if ambient air.

EXAMPLE 7

Preparation of Activator 7 (ASP 9)

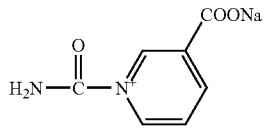

[ASP9]

Sodium cyanate (5 g, 0.077 mol) was dissolved in water (50 ml) and stirred for 5 minutes at room temperature; nicotinic acid solid (9.5 g, 0.077 mol) was gradually added to the stirred cyanate solution to keep pH maintained at 5~5.5 (no other acid was needed). After the addition of nicotinic acid, the reaction was continued at room temperature and at pH 5–5.5. When the pH of the solution became stable, the reaction was stopped. The product was precipitated by the addition of 400 ml of acetone to the mixture reaction; the solid was filtered off and dried in ambient air.

EXAMPLE 8

Preparation of Activator 8 (ASP 10)

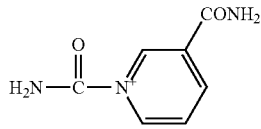

[ASP10]

Sodium cyanate (5 g, 0.077 mol) was dissolved in water (50 ml) and stirred for 5 minutes at room temperature; then the pH of the cyanate solution was adjusted to 5 using acetic acid. Nicotinic amide solid (12.2 g, 0.1 mol) was gradually added to the stirred cyanate solution over 1.5 hour, the pH was maintained at 5. After the addition of nicotinic amide, the reaction was continued at room temperature and at pH 5~5.5. When the pH became stable, the reaction was stopped. The product was precipitated by the addition of acetone (350 ml) to the reaction mixture; the solid was filtered off and dried in ambient air.

EXAMPLE 9

Preparation of Activator 9 (ASP11)

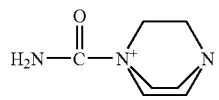 [ASP11]

Sodium cyanate (5 g, 0.077 mol) was dissolved in water (50 ml) and stirred for 5 minutes at room temperature; then the pH of the cyanate solution was adjusted to 5 using acetic acid. Solid diazabicyclooctane (DABCO) (8.6 g, 0.0077 mol) was gradually added to the stirred cyanate solution over 1 hour, the pH was maintained at 5. After the addition of DABCO, the reaction was continued at room temperature and at pH 5–5.5. When the pH became stable, the reaction was stopped. The product was precipitated by the addition of acetone (350 ml) to the reaction mixture; the solid was filtered off and dried in ambient air.

EXAMPLE 10

Tea Stained Cotton Fabric Bleaching Using Bleach Activators (ASP 7 to ASP 11) of Examples 5 to 9.

Tea-stained cotton fabric, the bleach method and conditions, were the same as those described in Example 4; but the CIE whiteness value of the tea-stained starting fabric was −52.4.

TABLE 4

CIE whiteness values of fabric bleached at pH 5 at different temperatures

| Bleaching Species | CIE Whiteness | | |
|---|---|---|---|
| | 20° C. | 50° C. | 95° C. |
| $H_2O_2$ | −27.3 | −2.3 | 33.9 |
| $H_2O_2$ + ASP 7 | −22.4 | 42.8 | 65.8 |
| $H_2O_2$ + ASP 8 | −25.3 | −4.8 | 52.1 |
| $H_2O_2$ + ASP 9 | −26.3 | −3.6 | 47.0 |
| $H_2O_2$ + ASP 10 | −29.8 | −5.5 | 31.5 |
| $H_2O_2$ + ASP 11 | −27.6 | −8.5 | 35.5 |

TABLE 5

CIE whiteness values of fabric bleached at pH 7 at different temperatures

| Bleaching Species | CIE Whiteness | | |
|---|---|---|---|
| | 20° C. | 50° C. | 95° C. |
| $H_2O_2$ | −0.3 | 5.3 | 67.5 |
| $H_2O_2$ + ASP 7 | 39.3 | 55.8 | 81.0 |
| $H_2O_2$ + ASP 8 | 7.7 | 40.7 | 81.2 |
| $H_2O_2$ + ASP 9 | 8.0 | 31.9 | 75.7 |
| $H_2O_2$ + ASP 10 | 0.2 | 8.4 | 69.3 |
| $H_2O_2$ + ASP 11 | 1.6 | 11.2 | 71.9 |

TABLE 6

CIE whiteness values of fabric bleached at pH 10 at different temperatures

| Bleaching Species | CIE Whiteness | | |
|---|---|---|---|
| | 20° C. | 50° C. | 95° C. |
| $H_2O_2$ | 23.1 | 54.4 | 70.6 |
| $H_2O_2$ + ASP 7 | 40.4 | 68.6 | 80.5 |
| $H_2O_2$ + ASP 8 | 31.4 | 62.1 | 83.5 |
| $H_2O_2$ + ASP 9 | 23.8 | 68.9 | 81.3 |
| $H_2O_2$ + ASP 10 | 21.7 | 60.2 | 76.9 |
| $H_2O_2$ + ASP 11 | 21.2 | 64.5 | 80.1 |

EXAMPLE 11

Raman Analysis of the Reaction between Hydrogen Peroxide and Carbamate (ASP 1 from Example 1).

Raman analysis of the reaction between ASP 1 (10% w/w) and hydrogen peroxide (10% w/w) at pH 6 showed percarbamic acid species formation, as characterised by absorption bands at 896 cm$^{-1}$, 876 cm$^{-1}$, and 853 cm$^{-1}$ (using secondary derivative analysis of the spectrum).

EXAMPLE 12

Tea-Stained Cotton Fabric Bleaching Using Sodium Cyanate and TAED (N, N, N', N'-tetraacetylethylenediamine ex Fluka Chemical, 95% grade).

Tea-stained cotton fabric, bleach solutions, conditions and the method of bleaching were the same as described in Example 4, but the CIE whiteness of the tea-stained starting fabric in these experiments was −30.8.

Bleach activators used were sodium cyanate and TAED.

TABLE 7

CIE whiteness values of fabric bleached at pH 5 at different temperatures

| Bleaching species | 20° C. | 50° C. | 95° C. |
|---|---|---|---|
| $H_2O_2$ | 0.6 | 23.1 | 60.8 |
| NaOCN + $H_2O_2$ | 24.8 | 67.6 | 83.4 |
| TAED + $H_2O_2$ | 5.8 | 46.6 | 76.6 |

TABLE 8

CIE whiteness values of fabric bleached at pH 7 at different temperatures

| Bleaching species | 20° C. | 50° C. | 95° C. |
|---|---|---|---|
| $H_2O_2$ | 13.6 | 36.6 | 81.0 |
| NaOCN + $H_2O_2$ | 51.4 | 78.2 | 84.1 |
| TAED + $H_2O_2$ | 49.8 | 76.6 | 79.8 |

TABLE 9

CIE whiteness values fabric bleached at pH 10 at different temperatures

| Bleaching species | 20° C. | 50° C. | 95° C. |
|---|---|---|---|
| $H_2O_2$ | 33.3 | 62.9 | 78.2 |
| NaOCN + $H_2O_2$ | 55.4 | 72.2 | 82.7 |

TABLE 9-continued

CIE whiteness values fabric bleached at pH 10 at different temperatures

| Bleaching species | 20° C. | 50° C. | 95° C. |
|---|---|---|---|
| TAED + $H_2O_2$ | 47.0 | 71.9 | 71.6 |

EXAMPLE 13

Raman Analysis of the Reaction Employing Sodium Cyanate and Hydrogen Peroxide.

Raman analysis of the reaction employing sodium cyanate (10% w/w) and hydrogen peroxide (10% w/w) at pH 8 showed percarbamic acid species formation as characterised by absorption bands at 896 cm$^{-1}$, 876 cm$^{-1}$ and 853 cm$^{-1}$ (second derivative spectra).

EXAMPLE 14

Tea-Stained Cotton Fabric Bleaching Using Sodium Cyanate, and TAED.

Tea-stained cotton fabric, bleach solutions, conditions and the method of bleaching were the same as described in Example 4, except the amount of bleach activator used (sodium cyanate, or TAED) was 0.1 g/l as opposed to 3 g/l in Example 4.

TABLE 10

CIE whiteness values of fabric bleached at pH 7 or 10 at 50°C.

| Bleaching species | pH 7 | pH 10 |
|---|---|---|
| $H_2O_2$ | 38.7 | 62.9 |
| $H_2O_2$ + NaOCN | 74.5 | 66.6 |
| $H_2O_2$ + TAED | 65.3 | 63.8 |

EXAMPLE 15

Tea-Stained Cotton Fabric Using Formamide

Tea-stained cotton fabric, the bleach method and conditions, were the same as those described in Example 4.

TABLE 11

CIE whiteness values of fabric bleached at 95° C. at different pH values

| | CIE Whiteness | |
|---|---|---|
| Bleaching Species | pH = 7 | pH = 10 |
| $H_2O_2$ | 69.6 | 79.5 |
| $H_2O_2$ + Formamide | 80.6 | 73.8 |

TABLE 12

CIE whiteness values of fabric bleached at 50° C. at different pH values

| | CIE Whiteness | | |
|---|---|---|---|
| Bleaching Species | pH = 5 | pH = 7 | pH = 10 |
| $H_2O_2$ | 35.6 | 43.6 | 60.3 |
| $H_2O_2$ + Formamide | 35.8 | 48.5 | 61.6 |

It will be seen from the above examples that certain bleach activators give optimal performance at particular pH and temperature conditions. Accordingly appropriate activators may be selected, having regard to the bleaching processes to be carried out. For example wool is generally bleached under near-neutral and mild conditions whereas cotton is generally bleached under alkaline high temperature conditions.

EXAMPLE 16

Bleaching of Dye Solutions

Dye solution was prepared by dissolving Remazol Black B (Dystar) (0.1 g) in water (1000 ml). For each sample 20 ml of the dye solution was used.

The bleaching solution was prepared as follows:

Dye solution 20 ml
Hydrogen peroxide 4 g
Bleach activator 2 g/l
pH 3, 7 or 10
Total volume 25 ml pH 3 was obtained with acetic acid; pH 7 was obtained with sodium dihydrogen phosphate (0.1M) and sodium hydroxide (0.1M); pH 10 was obtained using sodium carbonate.

The bleaching solutions were left at 20° C., and the absorbance values were measured after 3 hours and 24 hours using UV/visible spectrophotometry at 600 mm. The degree of dye removal or bleaching (R %) was calculated using the following equation:

$$\% R = 1 - (A_2/A_1) \times 100$$

where $A_1$ and $A_2$ are the absorbance values of the solution before and after bleaching.

The results are shown in the following tables.

TABLE 13

The degree of dye removal (% R) at pH 3 and 20° C.

| | 3 hours | | 24 hours | |
|---|---|---|---|---|
| Bleaching Species | Absorbance | % R | Absorbance | % R |
| $H_2O_2$ | 2.243 | 3.3 | 2.122 | 85 |
| NaOCN + $H_2O_2$ | 1.853 | 20.1 | 1.684 | 27.4 |
| TAED + $H_2O_2$ | 2.197 | 5.3 | 2.187 | 5.7 |
| Absorbance before bleach | | 2.320 | | |

TABLE 14

The degree of dye removal at pH 7 and 20° C.

| Bleaching Species | 3 hours | | 24 hours | |
|---|---|---|---|---|
| | Absorbance | % R | Absorbance | % R |
| $H_2O_2$ | 2.257 | 2.7 | 2.155 | 7.1 |
| $NaOCN + H_2O_2$ | 0.892 | 61.6 | 0.585 | 74.8 |
| $TAED + H_2O_2$ | 1.695 | 27.0 | 1.318 | 43.2 |
| Absorbance before bleach | | 2.320 | | |

TABLE 15

The degree of dye removal at pH 10 and 20° C.

| Bleaching Species | 3 hours | | 24 hours | |
|---|---|---|---|---|
| | Absorbance | % R | Absorbance | % R |
| $H_2O_2$ | 2.057 | 11.3 | 1.625 | 24.8 |
| $NaOCN + H_2O_2$ | 1.439 | 38.0 | 0.891 | 61.6 |
| $TAED + H_2O_2$ | 2.320 | 0.0 | 1.077 | 53.6 |
| Absorbance before bleach | | 2.320 | | |

EXAMPLE 17

Bleaching of Human Black Hair

The bleach solution was prepared as follows:
Hydrogen peroxide (100%) 1–3% W/W
Sodium cyanate 3–6% W/W
Ethylenediaminetetraacetic acid disodium salt, 2–3% V/V
D-gluconic acid 3% W/W
Balance water
pH 5

The human black hair tress was impregnated with this solution at 35° C. for 15–30 minutes, washed with tap water to remove residual bleach species and allowed to dry in air. The black hair was found to be bleached to a different blonde shade depending on the bleaching species concentration and bleach. If sodium cyanate was omitted, no bleaching effect was detected.

EXAMPLE 18

Cultures of *E. Coli* in Ringer's saline were exposed to various conditions for 45 minutes at 37° C. These were then serially diluted (eight 10-fold dilutions) and plated onto nutrient agar (treatments were done in triplicate to ensure reproducibility), and five tests were done overall as shown below. Initial *E. Coli* concentration was approximately $5 \times 10^9$/ml and cultures were grown in nutrient broth overnight before being centrifuged and then re-suspended in saline.
A *E. Coli* control—time zero.
B *E. Coli* control—time 45 minutes
C *E. Coli* plus peroxide at 5 g/l for 45 minutes
D *E. Coli* plus ASP 1 at 3 g/l for 45 minutes
E *E. Coli* plus peroxide of 5 g/l plus ASP 1 (3 g/l) for 45 minutes Plates were observed and counted after 2 days incubation at 37° C.
Counts recorded were as follows:—
A $40 \times 10^8$ colony forming units $ml^{-1}$
B $37 \times 10^8$ colony forming units $ml^{-1}$
C $12.9 \times 10^8$ colony forming units $ml^{-1}$
D $7.9 \times 10^8$ colony forming units $ml^{-1}$
E ~0 colony forming units $ml^{-1}$ (Results given are the averages of the three experiments and all of the replicates show very close agreement).

A and B were as expected about the same, C showed a moderate reduction (~66%) due to the presence of peroxide. D showed a reduction of about 80% due to ASP 1. E showed no bacterial growth, indicating 100% kill in the 45 minutes treatment period. In should be pointed out that in disinfecting bacteria, reductions in the order 90–99% are small, given the very large numbers which can be present to start with. The decrease in bacteria count in D may be due to toxicity of ASP 1 or possibly to the ASP 1 increasing the toxic effect of endogenously produced peroxide. Clearly the combination of peroxide and ASP 1 is highly effective. The above composition was also an effective bacteriocide against *pseudomonas aeruginosa, staphylococcus epidermis* and *aspergillus niger*.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except, combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extend to any novel one, or any novel combination, of the features disclosed in this specification (including any accompanying claims, abstract and drawings), or to any novel one, or any novel combination, of the steps of any method or process so disclosed.

What is claimed is:

1. A method of treatment of a material, comprising contacting said material with at least one of a percarbamic acid having the formula

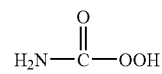

and a diacyl percarbamate having the formula

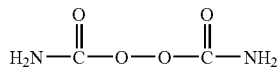

wherein the percabamic acid is generated by reacting a carbamate compound of the formula

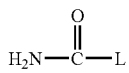 (II)

with hydrogen peroxide or the perhydroxy anion, and wherein L is a moiety displaced by the anion

and L is selected from the group consisting of a phosphonate, a phosphinate, thiourea, a quaternary ammonium group; a group of the formula —$SO_3M$ where M represents one of a hydrogen atom, an alkali metal atom, and an ammonium group; a group of the formula

—$XR^3$ where X represents an oxygen or sulphur atom and $R^3$ is selected from the group consisting of hydrogen, optionally substituted alkyl, optionally substituted aryl, optionally substituted amino, cyano, hydroxyl and optionally substituted alkylcarbonyl groups; and a group of the formula

—$Y(R^3)_2$ wherein each $R^3$ group is the same or different and is independently selected from the group consisting of hydrogen, optionally substituted alkyl, optionally substituted aryl, optionally substituted amino, cyano, hydroxyl and optionally substituted alkylcarbonyl groups, or the groups $R^3$ and Y together represent on of an optionally substituted heteroaryl group and an optionally substituted non-aromatic heterocyclic group.

2. A method as claimed in claim 1, wherein the at least one of percarbamic acid and diacyl percarbamate is in aqueous solution.

3. A method as claimed in claim 1, wherein the method of treatment is carried out in the pH range 3 to 11.

4. A method as claimed in claim 1, wherein the method of treatment is carried out at a temperature in the range 0° C. to 95° C.

5. A method as claimed in claim 1, wherein the material to be treated is selected from the group consisting of an organic fiber, an inorganic fiber a textile material, a metal surface, a wood surface, a ceramic surface, a plastics surface, a liquid, and an aqueous liquid.

6. A method as claimed in claim 1, wherein the method is a method of bleaching.

7. A method as claimed in claim 1, wherein the method is a method of sterilization of one of a surface and a contaminated aqueous solution.

8. A method as claimed in claim 1, wherein the at least one of percarbamic acid and diacyl percarbamate is generated in situ.

9. A method as claimed in claim 1, wherein L has the formula SX where X is selected from the group consisting of a cyano group, an optionally substituted $C_{1-6}$ alkyl group and $SO_3M$, where M represents one of a hydrogen atom, an alkali metal atom, and an ammonium group.

10. A method as claimed in claim 1, wherein L is —OX' where X' is selected from the group consisting of an optionally substituted alkyl group, an optionally substituted aryl group, an optionally substituted alkylcarbonyl group, a —CHO group and an —OCN group.

11. A method as claimed in claim 1, wherein L is —O—$PhSO_3M$, where M is selected from the group consisting of a hydrogen atom, an alkali metal atom, and an ammonium group.

12. A method as claimed in claim 1, wherein L is —NX"X'" where (i) X" and X'" are both alkyl groups or (ii) X" is a hydrogen atom and X'" is selected from the group consisting of cyano, alkyl, hydroxyl, amido, amino, aminosaccharide and a polyaminosaccharide group.

13. A method as claimed in claim 1, wherein L is of formula —P(═O)R'R" where R' represents a hydroxyl group and R" is selected from the group consisting of hydrogen, a hydroxyl group and an amido group.

14. A method as claimed in claim 1, wherein L is $Q^+$ connected to the C═O group by a positively charged N atom, the group Q being selected from the group consisting of a quaternary ammonium moiety formed from a tertiary amine, a heteroaryl group and a non-aromatic heterocyclic group.

15. A method as claimed in claim 1, where L is a group selected from the group consisting of:

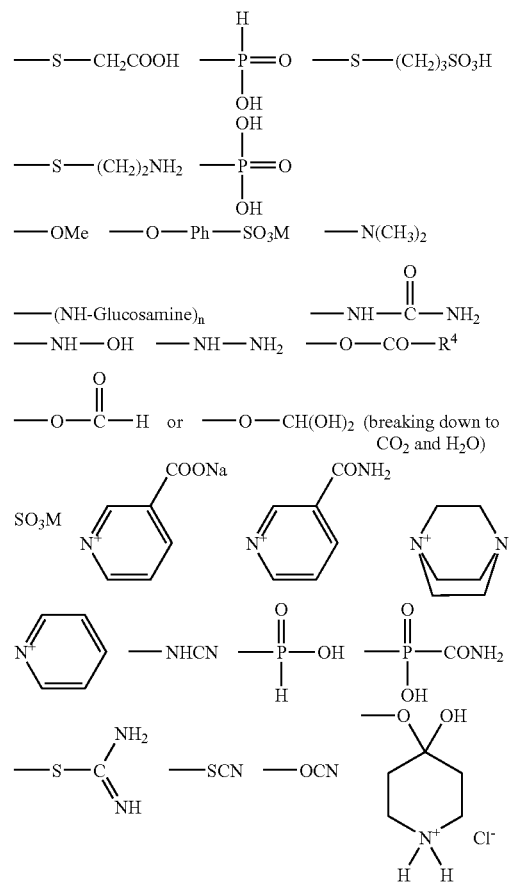

and wherein M is selected from the group consisting of a hydrogen atom, an alkali metal, and an ammonium group and where $R^4$ is one of an alkyl group and a hydrogen atom.

16. A method as claimed in claim 1, wherein the compound of formula (II) is prepared by a reaction of a reaction mixture comprising one of an alkali metal and an ammo nium cyanate, and a compound HL where L is a moiety displaceable by the perhydroxy anion.

17. A method as claimed in claim 16, wherein the compound of formula (II) is contacted with one of hydrogen peroxide and the perhydroxy anion, in situ.

18. A method as claimed in claim 16, wherein the pH of the reaction mixture is maintained between 2 and 10.

19. A composition comprising a compound of formula (II) as defined in claim 1 and one of hydrogen peroxide, the perhydroxy anion and a precursor therefor, wherein the composition is one of a washing composition, a bleaching composition, a sterilizing composition and a bactericidal composition.

20. A composition as claimed in claim 19, wherein the composition is one of a solid concentrate and a liquid concentrate.

21. A composition as claimed in claim 19, wherein the composition is a solid clothes washing composition, comprising a detergent, the compound of formula (II) and a compound which generates perhydroxy anions in water.

22. A compound of formula

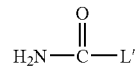

here L' represents a group selected from:

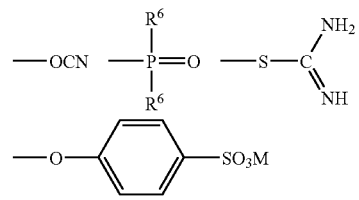

and
wherein each $R^6$ is independently selected from hydrogen, an amido group and a quaternary ammonium group.

* * * * *